(12) United States Patent
Saul et al.

(10) Patent No.: US 9,802,230 B2
(45) Date of Patent: *Oct. 31, 2017

(54) BIOREMEDIATION OF PERCHLORATE-CONTAMINATED MEDIA

(71) Applicants: Michael T. Saul, Cincinnati, OH (US); Jonathan Andrew Irwin, Wayland, MA (US)

(72) Inventors: Michael T. Saul, Cincinnati, OH (US); Jonathan Andrew Irwin, Wayland, MA (US)

(*) Notice: Subject to any disclaimer, the term of this patent is extended or adjusted under 35 U.S.C. 154(b) by 0 days.

This patent is subject to a terminal disclaimer.

(21) Appl. No.: 14/952,343

(22) Filed: Nov. 25, 2015

(65) Prior Publication Data

US 2016/0074916 A1    Mar. 17, 2016

Related U.S. Application Data

(63) Continuation of application No. 13/942,038, filed on Jul. 15, 2013, now Pat. No. 9,199,288.

(60) Provisional application No. 61/672,009, filed on Jul. 16, 2012.

(51) Int. Cl.
| | |
|---|---|
| *B09C 1/00* | (2006.01) |
| *C02F 3/34* | (2006.01) |
| *B09C 1/10* | (2006.01) |
| *C02F 3/02* | (2006.01) |
| *C02F 101/12* | (2006.01) |
| *C12R 1/40* | (2006.01) |
| *C02F 3/00* | (2006.01) |
| *C02F 103/06* | (2006.01) |

(52) U.S. Cl.
CPC .............. *B09C 1/10* (2013.01); *B09C 1/002* (2013.01); *C02F 3/02* (2013.01); *C02F 3/341* (2013.01); *C02F 3/348* (2013.01); *C02F 2003/001* (2013.01); *C02F 2101/12* (2013.01); *C02F 2103/06* (2013.01); *C02F 2209/06* (2013.01); *C02F 2209/22* (2013.01); *C02F 2305/06* (2013.01); *C12R 1/40* (2013.01); *Y02W 10/15* (2015.05)

(58) Field of Classification Search
None
See application file for complete search history.

(56) References Cited

U.S. PATENT DOCUMENTS 9,199,288 B2 * 12/2015 Saul .................... C02F 3/02

OTHER PUBLICATIONS

Interstate Technology Regulatory Council (IRTC), Technology Overview—Perchlorate: Overview of Issues, Status, and Remedial Options, Sep., 2005 (pp. 1-90), Appendix A (3 pages), Appendix B (3 pages), Appendix C (2 pages), Appendix D (5 pages), Appendix E (3 pages), Appendix F (33 pages), Appendix G (5 pages).
Krieg and Holt, editors, Bergey's Manual of Systematic Bacteriology, vol. 1, Lippincott, Williams & Wilkins, 1984, p. 156.
Nerenberg et al. Perchlorate Reduction in a Hydrogen-Based Membrane-Biofilm Reactor. Journal of the American Water Works Association, vol. 94 No. 4, (2002), pp. 103-114.
United States Environmental Protection Agency, Office of Solid Waste and Emergency Response, Technical Fact Sheet—Perchlorate, EPA 505-F-11-003, May 2012 (5 pages).
"CL-OUT" Trademark Electronic Search System (T.E.S.S.), 1999 (accessed Aug. 14, 2015), 1 page.

* cited by examiner

*Primary Examiner* — Chris R Tate
*Assistant Examiner* — Aaron J Kosar
(74) *Attorney, Agent, or Firm* — Thompson Hine LLP

(57) ABSTRACT

Methods for bioremediation of environmental media contaminated with at least one perchlorate compound. A *Pseudomonas* consortium of *P. putida* strain B, *P. putida* strain E, and *P. fluorescens* strain G was provided to contaminated water, soil, etc. under conditions to result in bioremediated water, soil, etc. In embodiments, the method is used ex-situ, e.g., in a reactor vessel, or is used in-situ.

20 Claims, 1 Drawing Sheet

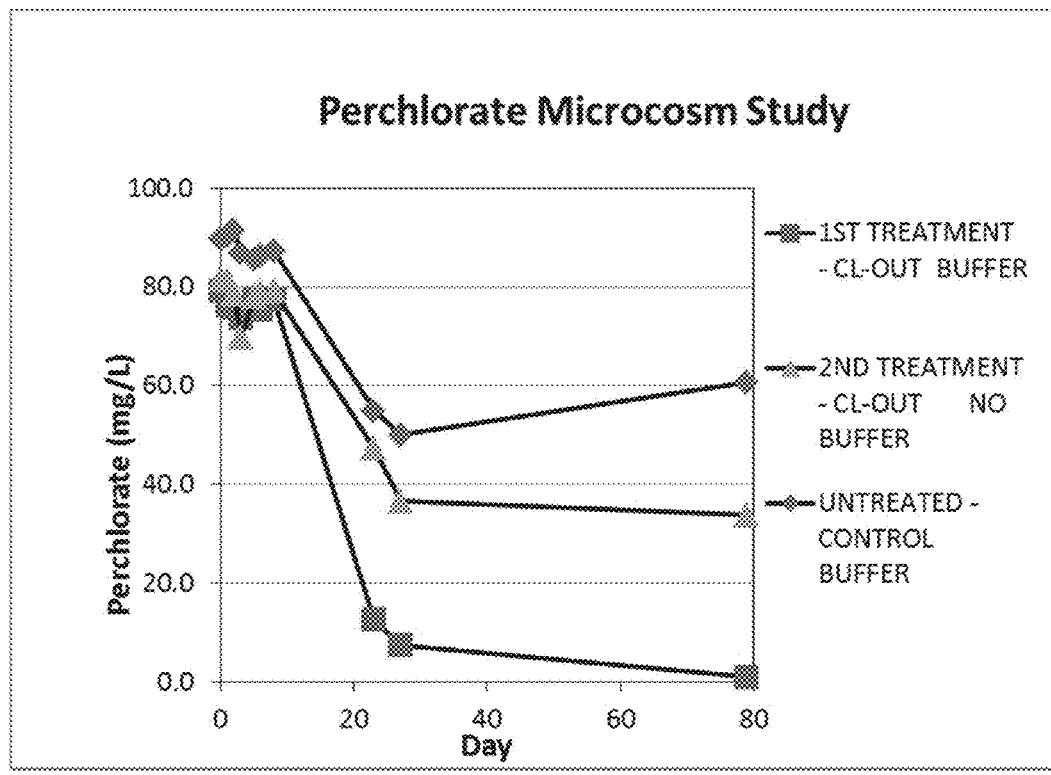

BIOREMEDIATION OF PERCHLORATE-CONTAMINATED MEDIA

This application is a Continuation of U.S. Ser. No. 13/942,038 filed Jul. 15, 2013, which claims priority to U.S. Ser. No. 61/672,009 filed Jul. 16, 2012, each of which is expressly incorporated by reference herein in its entirety.

Methods for removing or decreasing perchlorate ($ClO_4$) compounds in environmental media. In embodiments, the method provides ex-situ bioremediation or in-situ bioaugmentation.

Perchlorate is an oxidizer used as a component of propellants used in military, aerospace, and other applications (e.g., rocket fuel and fireworks), in blasting agents for mining and construction, and as a reagent in industrial chemical processing (USEPA 2012, p. 1). Sites that have been identified with higher concentrations of perchlorate contamination have typically involved manufacturing, testing, or disposal of solid rocket propellant; manufacturing of perchlorate compounds; and industrial manufacturing operations where perchlorate compounds were used as reagents. Based on the nature of these sources perchlorate contamination is also often found with comparable concentrations of dissolved nitrate (IRTC, 2005, p. 63). The environmental occurrence of perchlorate contamination within soil and groundwater presents both an environmental risk and a risk to human health, and thus requires treatment (USEPA 2012, p. 3).

Treatment with bioremediation has been used to degrade perchlorate in soil and water using microbes that are either native to the impacted media, or that are non-native and introduced to impacted media through bioaugmentation. Research has shown that perchlorate can be degraded by various microbial species, generally classified within the group *Proteobacteria*, which anaerobically reduce perchlorate to chlorite in reactions catalyzed by the enzyme perchlorate reductase (Nerenberg et al. Journal AWWA (2002) p. 202). Researchers have generally concluded that with those anaerobic microbes perchlorate is not biologically degraded in the presence of oxygen and that perchlorate may be biologically degraded only in the absence of oxygen (IRTC, 2005, p. 65). Creating persistent anaerobic conditions in situ within environmental media of soil and groundwater is a challenge. Because aerobes, such as *Pseudomonas*, are thought not to produce perchlorate reductase, they would not be thought to be able to degrade perchlorate which has chlorine in its highest oxidation state, chlorine (VII).

BRIEF DESCRIPTION OF THE DRAWING

FIG. 1 shows results of a perchlorate microcosm study plotting perchlorate concentration over time.

The invention has shown that a commercially available consortium of organisms, available as CL-Out® (CL Solutions, LLC Cincinnati Ohio) when applied to perchlorate-contaminated environmental media, degraded perchlorate and thus bioremediated the perchlorate-contaminated environmental media. The consortium did produce perchlorate reductase and does so in the presence of limited oxygen. CL-Out® is a consortium of *Pseudomonas* sp. including *Pseudomonas putida* and *Pseudomonas fluorescens*. Specifically, it includes *Pseudomonas putida* strain B (deposited with the Northern Regional Research Laboratory of the National Center for Agricultural Utilization Research, U.S. Department of Agriculture Agricultural Research Service, Peoria Ill., under accession number NRRL-B-18117), *Pseudomonas putida* strain E (deposited therein under accession number NRRL-B-18118) and *Pseudomonas fluorescens* strain G (deposited therein under accession number NRRL-B-18296). *Pseudomonas* sp. are widespread in the natural environment and *Pseudonmonas putida* and *Pseudomonas fluorescens* are generally considered non-pathogenic (Krieg and Holt, 1984, p. 156). Consequently, compositions such as CL-Out® may be used in bioreactors or introduced in bioaugmentation projects without risking the release of engineered or pathogenic microbial populations.

The consortium is available either in a lyophilized (freeze-dried) powder or in an aqueous suspension. In embodiments, the consortium is combined with a carbohydrate that serves as both an energy source and a reductant for the perchlorate anion. In one embodiment, the carbohydrate may be a polysaccharide such as sucrose; e.g., molasses, which has a carbohydrate content that is about 50% sucrose. In one embodiment, the carbohydrate may be a monosaccharaide such as dextrose; e.g., corn syrup or other starch-derived syrups and powders.

In one embodiment, the method may include the steps of providing an environmental medium containing a perchlorate compound to a reactor vessel, providing a consortium comprising *Pseudomonas putida* strain B, *Pseudomonas putida* strain E, and *Pseudomonas fluorescens* strain G to the reactor vessel, and providing a carbohydrate to the reactor vessel containing the consortium. If the environmental medium is saturated or unsaturated soil, the reactor vessel may be a batch or semi-batch reactor, and the environmental medium may be supplemented by adding water, and the carbohydrate may be supplied as a dilute solution in water. If the environmental medium is water, the reactor vessel may be a continuous or semi-batch reactor, and the reactor may or may not contain a solid or granular support matrix such as coarse sand, activated carbon, structured media, etc. The consortium within the reaction vessel metabolizes the carbohydrate to live and grow, with the perchlorate either serving as an oxidant, e.g., oxidizing dextrose and its metabolites and being reduced to one of chlorate (salt of chloric (pentavalent chlorine) acid), chlorite (salt containing the $ClO_3$ group), hypochlorite (salt or ester of hypochlorous acid HOCl), or chloride (salt of hydrochloric acid HCl), or being co-metabolically reduced to one of chlorate, chlorite, hypochlorite, or chloride during carbohydrate metabolism.

In one embodiment, the method may include the steps of providing a consortium comprising *Pseudomonas putida* strain B, *Pseudomonas putida* strain E, and *Pseudomonas fluorescens* strain G to an in situ environmental medium, and providing a carbohydrate to the in-situ environmental medium near the consortium. The environmental medium may be a saturated porous soil medium such as sand, or a flooding/flooded fractured bedrock medium such as sandstone or granite, or the vadose zone of a porous medium. In these examples, the environmental medium may be supplemented by adding water, e.g., the carbohydrate may be supplied as a dilute solution in water distributed over the medium, i.e., over the ground surface or into the subsurface through direct injection, injection wells, or structured infiltration or leaching systems or trenches. As in the reactor embodiments, the consortium metabolizes the carbohydrate to live and grow, with the perchlorate either serving as an oxidant, e.g., oxidizing dextrose and its metabolites and being reduced to one of chlorate, chlorite, hypochlorite, or chloride, or being co-metabolically reduced to one of chlorate, chlorite, hypochlorite, or chloride during carbohydrate metabolism.

In either embodiment, the consortium and the carbohydrate is provided in an amount or concentration sufficient to establish and maintain a substantial population of consortium microbes to effect bioremediation, e.g., within the reactor vessel, at the in-situ treatment site or zone, etc. In one embodiment, a target microbial population density is at least $10^6$ colony-forming-units (CFUs)/mL void volume. In one embodiment, a target carbohydrate concentration is 1 mg/mL void volume. A "void volume" is a simple volume in the event that the environmental media is groundwater and the reactor includes no solid or granular support matrix. One skilled in the art knows that for in-situ treatment, soil permeability must be sufficient to achieve effective and uniform distribution of the microbes throughout the impacted site or zone. One skilled in the art knows that the levels of dissolved oxygen (DO) must be sufficient to allow at least some aerobic metabolism by the consortium microbes.

To verify the method, i.e., that CL-Out® degraded perchlorate present in vadose zone soils and ground water, a field pilot study application of CL-OUT® to contaminated vadose soils and a microcosm study were performed (IRWIN Engineers, Inc. Natick Mass.) on groundwater samples obtained from an industrial site in Massachusetts where perchlorate waste had been released to the environment. The ground water samples contained 100 mg/L perchlorate and 560 mg/L nitrate.

Two treated groundwater samples were prepared as first and second treatment microcosms; a third untreated groundwater sample was maintained under otherwise identical conditions as a standard for comparison. The first and second microcosms were prepared with 1 gram/Liter of CL-OUT® bacteria and each of the three samples were applied with 23 grams/Liter of dextrose. Because of the low pH of the groundwater, the first treatment and untreated standard microcosms were buffered to neutral or slightly alkaline pH of 7.5-8 SU. To test the ability of the consortium to metabolize perchlorate under acidic conditions, the second treatment microcosm was not buffered and had an initial pH of 4-4.5 SU. Samples were taken from each microcosm immediately prior to treatment, daily for the first 7 days after treatment, and at 22, 27, 29, 31 and 80 days after treatment. Each sample was tested for perchlorate, pH, and dissolved oxygen.

| Day | pH (SU) | DO (mg/L) | Perchlorate (ppm) | Nitrate (mg/L) |
|---|---|---|---|---|
| FIRST TREATMENT - CL-OUT/DEXTROSE/BUFFER | | | | |
| 0 | 7.62 | 6.7 | 79.1 | |
| 1 | 7.74 | 0.4 | 76.4 | |
| 2 | 7.49 | 0.1 | 75.8 | |
| 3 | 7.42 | 0.1 | 73.8 | |
| 5 | 7.16 | 2.2 | 77.6 | |
| 6 | 7.03 | 0.9 | 75.5 | |
| 8 | 6.89 | 0.9 | 77.5 | |
| 23 | | | 12.6 | |
| 27 | 6.79 | 0.6 | 7.4 | ND[0.5] |
| 79 | | | 0.9 | |
| SECOND TREATMENT - CL-OUT/DEXTROSE/NO BUFFER | | | | |
| 0 | 4.38 | 7.4 | 81.6 | |
| 1 | 4.02 | 5.3 | 81.3 | |
| 2 | 3.95 | 7.0 | 78.5 | |
| 3 | 4.15 | 6.0 | 69.7 | |
| 5 | 4.14 | 4.8 | 77.9 | |
| 6 | 4.27 | 2.2 | 78.9 | |
| 8 | 4.37 | 2.8 | 79.2 | |
| 23 | | | 47.3 | |
| 27 | 6.2 | 0.3 | 36.6 | 0.68 |
| 79 | | | 33.7 | |
| UNTREATED - CONTROL - DEXTROSE/BUFFER | | | | |
| 0 | 7.53 | 8.1 | 89.6 | |
| 1 | 7.64 | 4.9 | 90.3 | |
| 2 | 7.89 | 3.1 | 91.4 | |
| 3 | 7.97 | 0.2 | 86.8 | |
| 5 | 8.02 | 0.4 | 85.5 | |
| 6 | 8.01 | 0.2 | 86.2 | |
| 8 | 8.09 | 0.7 | 87.3 | |
| 23 | | | 55.0 | |
| 27 | 8.63 | 2.8 | 50.0 | 41 |
| 79 | | | 60.6 | |

Referring to FIG. 1, perchlorate concentrations decreased in each of the three microcosms, but 99% reduction of perchlorate concentration in the first treatment was, by magnitude, greatly enhanced over the 33% perchlorate concentration reduction in the control without bioaugmentation. Likewise the 60% concentration reduction with the second treatment (unbuffered) with bioaugmentation was significantly greater than the control. The differential in results in the first and second treatment microcosms with the addition of CL-OUT® microbes and, particularly, in the first buffered treatment microcosm compared to the control was much greater than analytical variance and therefore statistically significant. Dentrification of nitrate was nearly complete in the bioaugmented microcosms, with concentrations in the first and second microcosms at 26 days reduced to less than 1 mg/L while in the untreated reactor the concentration was 10 mg/L indicating, as expected, that the CL-OUT® microbes consumed nitrates more effectively than the native population. Each microcosm exhibited a lag in the onset of perchlorate degradation however, the onset of perchlorate reduction was observed from 8 to 23 days.

Perchlorate concentration decreased by about 99% (from 80 mg/L to less than 1 mg/L) in the first treatment microcosm, by about 60% (from 80 mg/L to 32 mg/L) in the second treatment microcosm, and by only about 33% (from 90 mg/L to 60 mg/L) in the untreated standard microcosm. Initial perchlorate concentration in the first and second treatment microcosms was 80 mg/L versus 90 mg/L in the untreated standard microcosm. This is attributed to differences in dilution with preparation of solutions with and without the CL-OUT® addition and to the analytical method. Dissolved oxygen levels quickly decreased in the buffered microcosms over the first eight days. After 27 days, the dissolved oxygen level was lowest in the second treatment microcosm, slightly higher in the first treatment microcosm, and highest in the untreated standard microcosm. Dissolved oxygen was measurable in all three reactors throughout the study, confirming that aerobic to anoxic conditions were maintained during the test.

Each microcosm was sampled and tested for the presence of perchlorate reductase at the end of the test period. Perchlorate reductase was detected in the first, buffered and bioaugmented treatment microcosm, but was not detected in either the second bioaugmented treatment microcosm or in the untreated standard microcosm. We note that in both the second treatment and the untreated control, the pH increased during the first 26 days as would be expected with denitrification of nitrate, although nitrate remained measurable and further perchlorate reduction over the remaining period was not significant. That contrasted with the first treatment, where perchlorate reduction was achieved as pH decreased, nitrate was depleted to non-detect, and slow perchlorate reduction continued during the remainder of test period. Various factors may influence the temporal expression of perchlorate reductase including pH, nitrate concentration and dissolved oxygen.

Application of CL-OUT® to vadose zone soils was conducted in-situ at the known source area of the same site that provided the ground water samples for the treatability study. Perchlorate bearing waste water (3,500 mg/L) had leaked into the subsurface above the water table. An estimated volume of 30 cubic yards of impacted vadose zone soils were to be treated with the initial measured concentrations of perchlorate in soil at 1,800 mg/kg. The initial perchlorate concentration within underlying groundwater was measured at 0.3 mg/Liter. At day one ten gallons of a solution of CL-OUT® microbes (1 billion cfu/ml) and glucose (0.001%) with calcium carbonate for alkalinity were applied to the ground surface over the source point. At 30 days an additional five gallons of the same solution was applied. Groundwater was intermittently extracted adjacent to the source point and allowed to percolate through the soil column for 60 days. The pilot was stopped for winter conditions and pumping and percolation of groundwater recommenced on day 150. The soil was tested at 180 days and contained 8 mg/kg perchlorate. An additional five gallons of the same solution was applied and pumping continued through day 240 when the vadose soil was again tested. Soil testing results were an average concentration of 0.35 mg/kg perchlorate. Groundwater concentrations were monitored during the same period and measured concentrations were 0.2 mg/L and 0.1 mg/L respectively at 180 and 240 days. The decrease in perchlorate concentrations in both the soil and underlying ground water showed that the application of the CL-OUT® and dextrose solution removed perchlorate by bioremediation.

Following the source area treatment, a CL-OUT® bioaugmentation was applied to a larger area of perchlorate-containing ground water. Representative ground water samples of the larger area treatment showed perchlorate concentration decreased from 100 mg/L to 1.0 mg/L in eight months in the saturated soil media. In four months, the perchlorate concentration in ground water in the fractured bedrock decreased from a range of 2.0 to 7.0 mg/L to less than 0.01 mg/L. The large-scale application of CL-OUT® bioaugmentation to the perchlorate in groundwater verified applicability of the technique to environmental contamination.

These data demonstrated a novel approach to bioremediation of perchlorate using a consortium of *Pseudomonas* sp. While dissolved oxygen concentrations were reduced by carbohydrate metabolism, the disclosed method did not require an anaerobic environment to reduce perchlorate and, at least under neutral pH conditions, to produce and presumably use perchlorate reductase in metabolic reactions or to otherwise metabolize perchlorate in the presence of nitrates. Consequently, the CL-Out® consortium is a beneficial alternative to known *Proteobacterium* anaerobes, particularly at sites where groundwater dissolved oxygen levels remain high due to environmental factors and where nitrates are also present.

The following documents are expressly incorporated by reference herein in their entirety.

Interstate Technology Regulatory Council (IRTC), Technology Overview—Perchlorate: Overview of Issues, Status, and Remedial Options, September, 2005.

Krieg, N. R. and Holt, John G., editors, Bergey's Manual of Systematic Bacteriology, vol. 1, Lippincott, Williams & Wilkins, 1984.

Nerenberg, R., Rittmann, B. E., and Najm, I., Perchlorate Reduction in a Hydrogen-Based Membrane-Biofilm Reactor, Journal of the American Water Works Association, volume 94:11, November, 2002.

United States Environmental Protection Agency (USEPA), Office of Solid Waste and Emergency Response, Technical Fact Sheet—Perchlorate, EPA 505-F-11-003, May 2012.

The embodiments described in the specification are only specific embodiments of the inventor who is skilled in the art and are not limiting. Therefore, various changes, modifications, or alterations to those embodiments may be made without departing from the spirit of the invention or the scope of the following claims.

What is claimed is:

1. A method for decreasing an amount of at least one perchlorate compound in a contaminated environmental medium, the method comprising the steps of:
    (a) contacting an effective amount of a consortium culture of *Pseudomonas putida* strain B, *Pseudomonas putida* strain E, and *Pseudomonas fluorescens* strain G with the contaminated environmental medium; and
    (b) providing a carbohydrate to the consortium-contacted medium of step (a) under conditions that result in a decreased amount of the at least one perchlorate compound in the environmental medium.

2. The method of claim 1 wherein step (a) occurs in-situ.

3. The method of claim 1 wherein step (a) occurs ex-situ.

4. The method of claim 1 wherein the environmental medium is soil.

5. The method of claim 4 wherein the environmental medium is supplemented with water.

6. The method of claim 4 wherein the soil is a saturated porous soil.

7. The method of claim 4 wherein the soil is an unsaturated porous soil.

8. The method of claim 7 wherein the unsaturated porous soil is supplemented with water.

9. The method of claim 1 wherein the environmental medium is water.

10. The method of claim 9 wherein step (a) further comprises a solid or granular support matrix in contact with the contaminated environmental medium.

11. The method of claim 1 wherein the carbohydrate is a polysaccharide.

12. The method of claim 1 wherein the carbohydrate is a monosaccharaide.

13. The method of claim 12 wherein the monosaccharaide is dextrose.

14. The method of claim 13 wherein dextrose is provided at a concentration of 1 mg/mL void volume of said environmental medium.

15. The method of claim 1 wherein the consortium is provided at a concentration of at least $10^6$ colony-forming-units (CFUs)/mL void volume of said environmental medium.

16. The method of claim 1 wherein the environmental medium is groundwater saturated bedrock.

17. The method of claim 1 further comprising the step of (c) providing supplemental nitrate to the consortium-contacted medium of step (a).

18. The method of claim 1 wherein the carbohydrate is provided at a concentration effective for the consortium culture to maintain at least a limited concentration of dissolved oxygen (DO).

19. The method of claim 18 wherein the carbohydrate is provided at a concentration effective for the consortium culture to maintain a limited concentration of dissolved oxygen (DO), the DO concentration sufficient for aerobic metabolism in at least a portion of the consortium.

20. The method of claim 1 wherein step (b) results in the at least one perchlorate compound being removed from the contaminated environmental medium.

\* \* \* \* \*